United States Patent [19]

de Toledo

[11] Patent Number: 5,184,627

[45] Date of Patent: * Feb. 9, 1993

[54] INFUSION GUIDEWIRE INCLUDING PROXIMAL STIFFENING SHEATH

[75] Inventor: Fernando A. de Toledo, Concord, Mass.

[73] Assignee: Boston Scientific Corporation, Watertown, Mass.

[*] Notice: The portion of the term of this patent subsequent to Jan. 12, 2010 has been disclaimed.

[21] Appl. No.: 644,156

[22] Filed: Jan. 18, 1991

[51] Int. Cl.$^5$ ............................................. A61B 5/00
[52] U.S. Cl. ................................. 128/772; 604/164; 604/264; 604/282
[58] Field of Search ............... 128/772, 656, 657, 658; 604/264, 280, 282, 164

[56] References Cited

U.S. PATENT DOCUMENTS

| | | |
|---|---|---|
| 4,362,163 | 12/1982 | Krick .................................. 604/280 |
| 4,538,622 | 9/1985 | Samson et al. ...................... 128/772 |
| 4,739,768 | 4/1988 | Engelson ............................. 128/658 |
| 4,834,709 | 5/1989 | Banning et al. ..................... 604/170 |
| 4,846,186 | 7/1989 | Box et al. ............................ 128/657 |
| 4,906,241 | 3/1990 | Noddin et al. ...................... 606/194 |
| 4,955,862 | 9/1990 | Sepetka .............................. 604/164 |

Primary Examiner—Max Hinderburg
Assistant Examiner—Guy V. Tucker
Attorney, Agent, or Firm—Don Halgren

[57] ABSTRACT

A flexible elongated medical infusion guidewire having proximal and distal portions for delivering a pressurized fluid medicaments to a site with a body vessel. The guidewire is comprised of a helically wound coil having a polyimide sheath tightly enclosing its proximal portion, and a teflon sheath tightly covering the entire wire coil. The teflon sheath is punctured at its distal end to facilitate release of fluid therethrough. The coil is closed at its distalmost end by a ball weld.

19 Claims, 1 Drawing Sheet

INFUSION GUIDEWIRE INCLUDING PROXIMAL STIFFENING SHEATH

BACKGROUND OF THE INVENTION

1. Field of the Invention

This invention relates generally to guidewires and catheters utilized in medical procedures, and more particularly to an infusion wire.

2. Description of the Prior Art

Intravenous infusion is generally done by catheters for delivering a parenteral liquid into the blood stream of a patient. The catheters are generally formed with a single liquid outlet at the catheter distal tip.

An early patent showing a catheter for introducing liquid into a body is shown in U.S. Pat. No. 623,022 to Johnson. The Johnson catheter shows a coil which is disposed in a sheath. The sheath has a proximal and a distal end. The distal end has a plurality of holes therein. A coil is disposed within the sheath, a lumen disposed within the coil. Liquid is passed through the lumen and out through the coil and the holes in the distal end of the sheath of the catheter.

An arrangement for the collection of bodily fluids is shown in a valved catheter device in U.S. Pat. No. 3,841,308. As shown therein, it comprises a helical coil having a proximal and a distal end, the distal end blocked by a ball tip. The ball tip is attached to a stylet. The helical coil is covered by a sheath, having a plurality of holes in its distalmost end. The helical coil has an innermost lumen in fluid communication with the holes in the sheath. A further catheter assembly for the release of fluid within a vessel, is shown in U.S. Pat. No. 4,318,402. This catheter assembly provides for an infusion, by an arrangement of an outer catheter enclosing an inner catheter. The inner catheter discharges fluid into the outer catheter, with a plurality of holes within the outer catheter causing infusion of the fluid therebeyond.

The co-pending patent application of inventor, Ser. No. 07/605,561 is also referenced here.

BRIEF SUMMARY OF THE INVENTION

It is an object of the present invention to provide a guidewire having catheter-like characteristics which permits infusion of fluid medicaments right into a blood clot or occlusion in the vessel of a patient, through a guidewire. It is a further object of this invention to obviate the use of a catheter, through the use of a helically coiled guidewire, capable of infusing chemotherapeutic drugs directly within a situs. The infusing wire comprises an inner multifilar round wire winding of generally constant diameter having a distal end and a proximal end. The proximal portion of the helical coil is covered with a polyimide tubing and may have a radioopaque band disposed distal to the polyamide tubing and disposed around the helical multifilar coil. A second outermost teflon sheath is disposed over the entire helical coil from the proximal to the distalmost end. The distal end of the coil has a ball weld thereon. The distal portion of the coil, wherein it is covered by only a teflon sheath, is defined as the "weep" area. The weep area has perforations through the teflon sheath. A therapeutic fluid agent may be pressurized and directed into the proximal end of the wire through an appropriate hub or fitting, which therapeutic agent is permitted to travel through the lumen and diffuse out through the distal portion of the helical coil through the appropriate weep holes in the teflon sheath therearound.

BRIEF DESCRIPTION OF THE DRAWINGS

The objects and advantages of the present invention will become more apparent when viewed in conjunction with the following drawings, in which.

DESCRIPTION OF THE PREFERRED EMBODIMENTS

Figure 1:
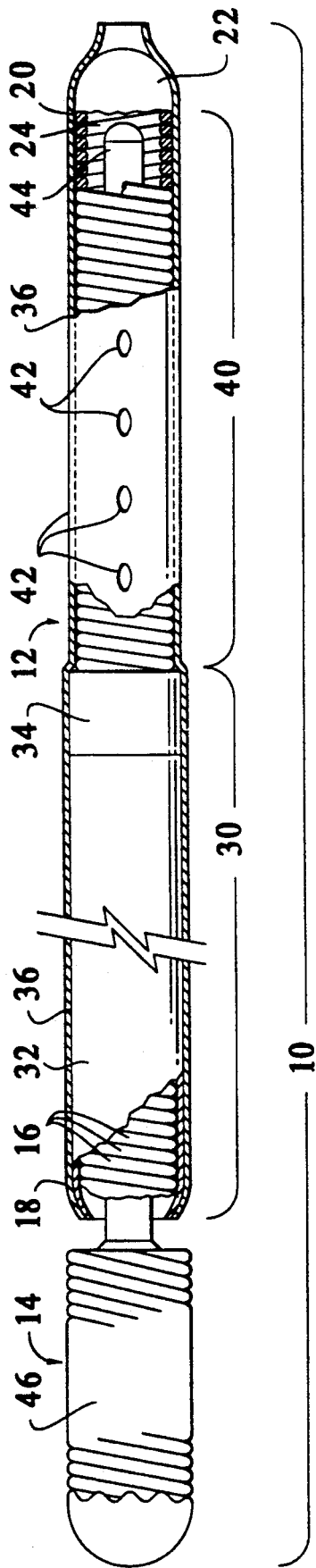
FIG. 1 is a longitudinal cross sectional view taken of a infusion wire and its attendant removable core.

Referring to the drawings in detail, and particularly to FIG. 1, there is shown an infusion wire assembly 10. The infusion wire assembly 10 comprises an infusion wire 12 and a removable stiffening core 14.

The infusion wire 12 is comprised of a helically disposed multifilar array of wires 16, which have been wrapped about a mandrel, not shown. The infusion wire 12 has a proximal end 18 and a distal end 20. A ball weld 22 is adapted onto the distalmost tip of the infusion wire 12 as shown in FIG. 1.

The multifilar array of wires 16 are disposed at a pitch angle of about 15° to 18° with respect to the longitudinal axis of the infusion wire 12. The wires 16 define a lumen 24 therewithin. Each wire of the multifilar array of wires 16 is round and is of about 0.005 inches in diameter. Each wire of the multifilar array of wires 16 is made from stainless steel.

The infusion wire 12 has a stiffened proximal portion 30, which is comprised of the helical multifilar array of wires 16 arranged within a polyimide sheath 32 of overall diameter of about 0.035 cm. The stiffened proximal portion 30 preferably extends for about 90 to 95 percent of the full length (about 145 cm) of the infusion wire 12. The polyimide sheath 32 is about 0.0015 inches thick, and is of corset fit about the wires 16.

A band of tantalum 34 may be disposed about the wires 16, to mark the proximal end of the distal portion 40. The tantalum band 34 is a radiopaque marker utilized by the physician to determine the location of the infusion wire 12, under fluoroscopic examination of a patient in which the infusion wire 12 has been inserted.

The entire length of the infusion wire 12 is corsetted by an enclosure sheath of teflon 36 which has been shrunk fit over the polyimide sheath 32, the tantalum band 34 when utilized, and a distalmost portion 40 of the helical array of wires 16 and the ball weld 22, as shown in FIG. 1. The sheath of teflon 36 is shrunk fit just distally beyond the ball weld 22, so as to provide a mechanical grip thereover, to minimize the likelihood of any peelback of the sheath 36 over the ball weld 22, effecting infusion thereof. The teflon sheath 36 is about 0.0015 inches thick and is the only covering for the distalmost portion 40 of wires 16. This distalmost portion 40 of teflon "only" covered wires is identified as the "weep" region of the infusion wire 12, and preferably extends from about 3 cm. to about 15 cm. from the distalmost end, which is about 10 percent of the length of the wire 12.

The teflon 36 in the "weep" region 40 has a plurality of pre-punched holes 42 about 0.010 inches in diameter. The holes 42 may be spirally arrayed about the "weep" region 40 through the teflon sheath 36 thereat. The holes 42 are wide enough in diameter to extend across and expose at least two windings of the wire 16.

The removable stiffening core 14, displacable through the lumen 24, is comprised of an elongated stylet 44 which extends almost the entire length of the infusion wire 12. The stylet 44 has a distal end which is spaced from the inside of the ball weld 22 when the stiffening core 14 is fully engaged into the infusion wire 12. A handle 46 is secured to the proximal end of the stylet 14 to permit axial displacement/adjustment of the stiffening core 14 within the infusion wire 12.

Figure 2:
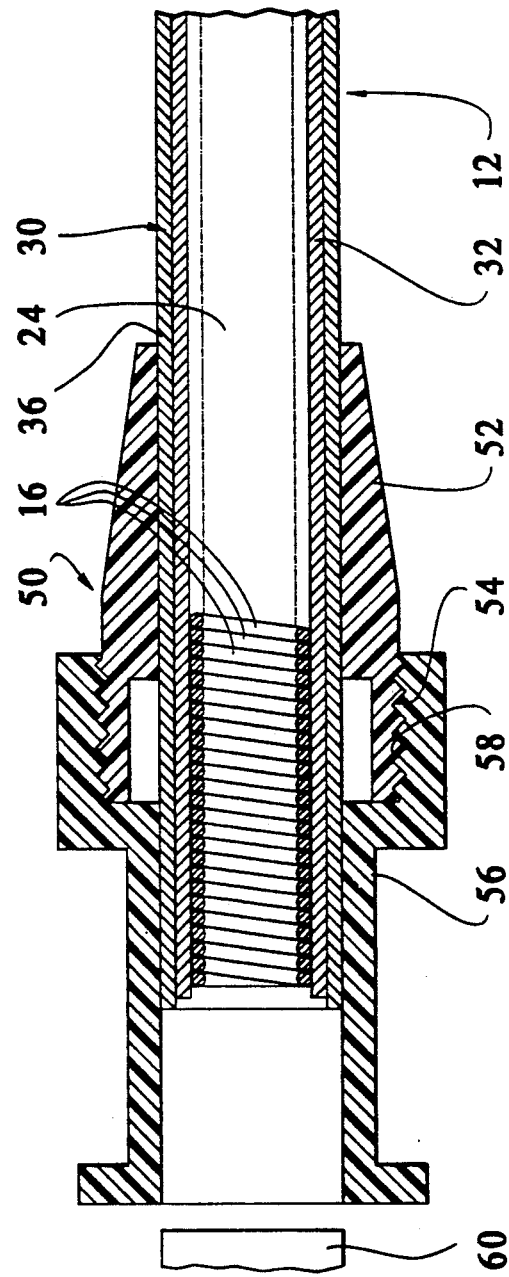
FIG. 2 is a cross sectional view of the proximal end of the infusion wire adapted with a hub end lock assembly, for enabling receipt of a medicament fluid therein.

A typical hub adapter 50 is shown on the proximal end of the infusion wire 12, in FIG. 2. A ferrule 52 is in a tight fitting relationship about the teflon sheath 36. The ferrule 52 has external threads 54 on the proximal end thereof. A cylindrical body 56 having a threaded female surface 58 on its distal end, engages the external threads 54. A conduit 60 is matable with the body 56 to permit fluid communication from the conduit 60 and the lumen 24 of the infusion wire 12. A connector arrangement of this type may be a luer lock, for engaging lumens in a communicable relationship.

Thus what has been shown is a novel guidewire for adaptation of infusion means into a site within a body vessel. The flexible infusion guidewire is made from at least one helically wound coil of stainless steel type wire having proximal and distal portions. The proximal portion of the coil is disposed within an inner sheath of thin polyimide material for "stiffening" purposes thereof. The proximal portion and the distal portion of the coil each being also fully disposed within a thin enclosure sheath of polytetrafluroethylene, commonly known as teflon, the distalmost end of the coil having a passage (lumen) blocking ball weld thereon, the distal portion of the teflon sheath having openings punctured therein for dispersion of any pressurized fluids from the lumen within the coil, to "weep into" the site into which the infusion guidewire may be pushed.

I claim:

1. A flexible elongated medical infusion guidewire having proximal and distal portions, adapted for delivering pressurized fluid medicaments to a site within a body vessel, comprising:
   a flexible elongated helically arranged coil of round wire having a proximal portion and a distal portion, and defining a central lumen therethrough having a distalmost end blocked by a ball weld thereon;
   a first sheath stiffening means comprised of a single flexible layer or polyimide film in a tubular configuration disposed immediately about and co-extensive with substantially all of just said proximal portion of just said helically arranged coil;
   a second sheath enclosure means disposed immediately about said first sheath means and being co-extensive therewith and with all of said distal portion of said helically arranged coil; and
   a plurality of dispersion means arranged within said distal portion of said second sheath.

2. A flexible elongated medical infusion guidewire as recited in claim 1, wherein a radiopaque band is disposed at the distalmost end of said first sheath means on the proximal portion of said guidewire.

3. A flexible elongated medical infusion guidewire as recited in claim 1, wherein said second sheath means comprises a single flexible layer of polytetrafluroethylene of tubular configuration, in tight intimate contact with said first sheath means in said proximal portion of said guidewire and in tight intimate contact with said helically wound coils in said distal portion of said guidewire.

4. A flexible elongated medical infusion guidewire as recited in claim 3, including an elongated movable stiffening core adapted to be longitudinally displaced within said lumen, and removable therefrom.

5. A flexible elongated medical infusion guidewire as recited in claim 3, including an engagable hub disposed upon the proximal end of said infusion guidewire for adaptation of said lumen to a pressurized fluid source for supply of medical infusion fluid thereto.

6. A flexible elongated medical infusion guidewire as recited in claim 3, wherein said radiopaque band is made from tantalum.

7. A flexible elongated medical infusion guidewire as recited in claim 3, wherein said helically arranged coil is a multifilar winding.

8. A flexible elongated medical infusion guidewire as recited in claim 3, wherein said helically arranged coil is comprised of a single layer of said wire.

9. A flexible elongated medical infusion guidewire as recited in claim 3, wherein said second sheath is heat shrunk onto said first sheath means and said distal portion of said infusion guidewire.

10. A flexible elongated medical infusion guidewire as recited in claim 1, wherein said dispersion means comprises puncture holes arranged only through said second sheath means only at the distal portion of said guidewire.

11. A flexible elongated medical infusion guidewire as recited in claim 1, wherein said helically arranged coil of round wire is made from stainless steel.

12. A flexible elongated medical infusion guidewire as recited in claim 11, wherein said stainless steel wire is about 0.005 inches in diameter.

13. A flexible elongated medical infusion guidewire having proximal and distal portions adapted for delivering pressurized fluid medicaments to a site within a body vessel, comprising:
   a flexible elongated multifilar coil of helically wound round wire defining a central lumen therethrough having a closed distalmost end;
   a first and a second sheath closely fitted completely about a proximal portion of said multifilar coil;
   said second sheath closely fitted about and extending completely over the balance of said coil comprising a distal weeping portion of said multifilar coil; and
   an indicator band arranged at the distal end of said first sheath and under said second sheath, to provide marker means as to the location of said guidewire in a body vessel.

14. A flexible elongated infusion guidewire as recited in claim 13, wherein said first sheath comprises a flexible tubing of polyimide material about 0.0015 inches thick, and said second sheath comprises a flexible tubing of tetrafluoroethylene about 0.0015 inches thick.

15. A flexible elongated infusion guidewire as recited in claim 13, wherein said distal portion of said infusion guidewire comprises no more than about ten percent of the length of said guidewire.

16. A flexible elongated infusion guidewire as recited in claim 13, wherein said distal portion of said second sheath on said guidewire is foraminous.

17. A flexible elongated infusion guidewire as recited in claim 13, wherein said proximal portion of said coil is covered only with said first sheath and said second sheath, and said distal portion of said coil is covered only by a heat shrunk second sheath.

18. A flexible elongated infusion guidewire as recited in claim 13, wherein said closed distalmost end comprises a ball weld attached to said coil thereat.

19. A flexible elongated infusion guidewire as recited in claim 18, wherein said second sheath is heat shrunk around the distalmost portion of said ball weld so as to provide a gripping means thereon to eliminate any peeling back of said second sheath from the closed distal end.

* * * * *